United States Patent
Alshafei et al.

(10) Patent No.: US 10,407,363 B2
(45) Date of Patent: Sep. 10, 2019

(54) STEAM-LESS PROCESS FOR CONVERTING BUTENES TO 1,3-BUTADIENE

(71) Applicant: Saudi Arabian Oil Company, Dhahran (SA)

(72) Inventors: Faisal H. Alshafei, Khobar (SA); Miao Sun, Dhahran (SA); Munir D. Khokhar, Dammam (SA); Zhonglin Zhang, Dhahran (SA); Sohel K. Shaikh, Dhahran (SA); Mark P. Kaminsky, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/678,405

(22) Filed: Aug. 16, 2017

(65) Prior Publication Data

US 2019/0055175 A1    Feb. 21, 2019

(51) Int. Cl.
*C07C 5/48* (2006.01)
*B01J 8/02* (2006.01)
(Continued)

(52) U.S. Cl.
CPC .............. *C07C 5/48* (2013.01); *B01J 8/0278* (2013.01); *B01J 21/10* (2013.01); *B01J 23/30* (2013.01);
(Continued)

(58) Field of Classification Search
CPC ... C07C 5/48; C07C 2521/08; C07C 2521/10; C07C 2523/30; B01J 35/0006;
(Continued)

(56) References Cited

U.S. PATENT DOCUMENTS 3,159,688 A * 12/1964 Jennings .................. B01J 23/24
502/215
3,732,327 A * 5/1973 Pitzer ....................... B01J 23/14
502/208
(Continued)

FOREIGN PATENT DOCUMENTS

CN      105749931 A    7/2016
WO   2008153643 A1   12/2008
(Continued)

OTHER PUBLICATIONS

Partial International Search for related PCT application PCT/US2018/000279 dated Dec. 19, 2018; pp. 1-13.
(Continued)

*Primary Examiner* — Brian A McCaig
*Assistant Examiner* — Jason Y Chong
(74) *Attorney, Agent, or Firm* — Bracewell LLP; Constance G. Rhebergen; Brian H. Tompkins (57) ABSTRACT

Processes, systems, and catalysts for the conversion of 2-butene to 1,3-butaidene without the use of steam or, in some embodiments, with a reduced use of steam as compared to prior art processes are provided. The catalyst includes tungsten trioxide ($WO_3$) on an inorganic support includes activated magnesium oxide (MgO) and may be referred to as a "dual catalyst" or a "co-catalyst." Embodiments of the catalyst. A process for the production of 1,3-butadiene may include contacting a feed stream of 2-butene with a $WO_3$-inorganic support catalyst or a MgO and $WO_3$-inorganic support catalyst and may be performed without steam in the feed stream.

13 Claims, 2 Drawing Sheets

(51) Int. Cl.
  *B01J 21/10* (2006.01)
  *B01J 23/30* (2006.01)
  *B01J 35/00* (2006.01)
  *B01J 35/10* (2006.01)
  *B01J 37/02* (2006.01)
  *B01J 37/08* (2006.01)

(52) U.S. Cl.
  CPC ....... *B01J 35/0006* (2013.01); *B01J 35/1014* (2013.01); *B01J 35/1019* (2013.01); *B01J 35/1038* (2013.01); *B01J 35/1042* (2013.01); *B01J 37/0205* (2013.01); *B01J 37/082* (2013.01); *B01J 2208/024* (2013.01); *C07C 2521/08* (2013.01); *C07C 2521/10* (2013.01); *C07C 2521/14* (2013.01); *C07C 2523/30* (2013.01)

(58) Field of Classification Search
  CPC .......... B01J 35/1014; B01J 35/1019; B01J 35/1038; B01J 35/1042; B01J 8/0278; B01J 21/10; B01J 23/30; B01J 2208/024; B01J 37/082; B01J 37/0205
  See application file for complete search history.

(56) References Cited

U.S. PATENT DOCUMENTS

| | | | |
|---|---|---|---|
| 3,895,051 A | 7/1975 | Umemura et al. | |
| 3,915,897 A | 10/1975 | Reusser et al. | |
| 3,940,346 A * | 2/1976 | Zuech | B01J 31/143 502/117 |
| 4,164,519 A * | 8/1979 | Bertus | B01J 23/20 585/622 |
| 4,225,738 A | 9/1980 | Cihonski | |
| 4,777,319 A | 10/1988 | Kung et al. | |
| 6,040,489 A | 3/2000 | Imai | |
| 6,420,619 B1 | 7/2002 | Gartside et al. | |
| 8,252,150 B1 | 8/2012 | Hsu et al. | |
| 8,586,813 B2 | 11/2013 | Ramachandran et al. | |
| 9,040,764 B2 | 5/2015 | Ramachandran et al. | |
| 9,199,895 B2 | 12/2015 | Cha et al. | |
| 2010/0167911 A1 | 7/2010 | Shum | |
| 2011/0245568 A1 | 10/2011 | Khabashesku et al. | |
| 2013/0209351 A1 | 8/2013 | Shin et al. | |
| 2014/0163291 A1 | 6/2014 | Grune et al. | |
| 2014/0200379 A1 | 7/2014 | Josch et al. | |
| 2014/0200380 A1 | 7/2014 | Josch et al. | |
| 2015/0141721 A1 | 5/2015 | Choi et al. | |
| 2015/0151292 A1 | 6/2015 | Suh et al. | |
| 2016/0122264 A1 | 5/2016 | Olbert et al. | |
| 2016/0152531 A1 | 6/2016 | Walsdorff et al. | |
| 2016/0355450 A1 | 12/2016 | Grune et al. | |

FOREIGN PATENT DOCUMENTS

| | | |
|---|---|---|
| WO | 2010137595 A1 | 12/2010 |
| WO | 2013113743 A1 | 8/2013 |
| WO | 2015004042 A2 | 1/2015 |
| WO | 2015007839 A1 | 1/2015 |
| WO | 2015087668 A1 | 6/2015 |
| WO | 2017003821 A1 | 1/2017 |

OTHER PUBLICATIONS

International Search Report and Written Opinion for related PCT application PCT/US2018/000279 dated Feb. 14, 2019; pp. 1-17.

* cited by examiner

STEAM-LESS PROCESS FOR CONVERTING BUTENES TO 1,3-BUTADIENE

BACKGROUND

Field of the Disclosure

The present disclosure generally relates to the production of butadiene. More specifically, embodiments of the disclosure relate to the catalytic conversion of butene to 1,3-butadiene.

Description of the Related Art 1,3-Butadiene (also referred to as simply "butadiene" or "1,3-BD") is an important industrial chemical used as a predecessor and a building block for many materials. 1,3-butadiene is used in various industries including construction, healthcare, consumer durables, and automotive. Major butadiene derivatives include acrylonitrile butadiene styrene (ABS), styrene butadiene rubber (SBR), nitrile butadiene rubber (NBR), and hexamethylenediamine.

A significant portion of the 1,3-butadiene produced is used in the manufacturing of synthetic rubber. The automotive industry heavily relies on butadiene for the manufacturing of tires and other parts. The recent growth of the automotive industry in locations such as China, India, and Brazil has played a pivotal role in increasing the demand for 1,3-butadiene in the market. The trends of growth in demand and decrease in supply may result in a rise in the prices of 1,3-butadiene and an increase in the price volatility.

SUMMARY

Currently, almost all 1,3-butadiene is produced as a byproduct of ethylene steam cracking of naphtha feedstock, gasoil feedstock, or both. The switch to lighter feedstocks has reduced the amount of 1,3-butadiene available from ethylene cracking to such an extent that the reduced amount of 1,3-butadiene that is produced cannot sometimes be economically recovered. Additionally, the steam cracking processes require a significant amount of steam diluent in the feed stream to remove coke. This reduced production presents a demand for on-purpose 1,3-butadiene technologies including—but not limited to—n-butane dehydrogenation and mixed butenes oxidative dehydrogenation.

In one embodiment, a method for producing 1,3-butadiene is provided. The method includes receiving a feed stream that includes 2-butene and contacting the feed stream with a catalyst in the presence of an oxidant to convert the 2-butene to 1-3-butadiene, the catalyst including tungsten oxide impregnated on an inorganic support. In some embodiments, the feed stream does not include steam. In some embodiments, the oxidant includes air. In some embodiments, the contacting is performed at a temperature in the range of 400° C. to 550°. In some embodiments, the feed stream includes 1-butene. In some embodiments, the inorganic support includes silica. In some embodiments, the catalyst includes magnesium oxide. In some embodiments, the magnesium oxide has a surface area in the range of 30 meters-squared/gram (m$^2$/g) to 200 m$^2$/g. In some embodiments, the catalyst includes a first layer of the tungsten oxide impregnated on the inorganic support, a second layer of the tungsten oxide impregnated on the inorganic support, and a layer of the magnesium oxide positioned between the first layer and the second layer. In some embodiments, the catalyst includes a layer of the magnesium oxide disposed on a layer of the tungsten oxide impregnated on the inorganic support. In some embodiments, the volumetric ratio of the magnesium oxide to the tungsten oxide impregnated on the inorganic support is in the range of 1:3 to 3:1. In some embodiments, contacting the feed stream, at a temperature in the range of 400° C. to 550°, with a catalyst to convert the 2-butene to 1-3-butadiene achieves a 1,3-butadiene selectivity of at least 23.

In another embodiment, a system for producing 1,3-butadiene is provided. The system includes a reactor and a catalyst positioned in the reactor and having tungsten oxide impregnated on an inorganic support, the reactor configured to receive a feed stream that includes 2-butene and contact the feed stream at a temperature in the range of 400° C. to 550° C. with the catalyst in the presence of an oxidant to convert the 2-butene to 1-3-butadiene. In some embodiments, the feed stream does not include steam. In some embodiments, the oxidant includes air. In some embodiments, the reactor is a fixed bed continuous flow reactor. In some embodiments, the feed stream includes 1-butene. In some embodiments, the inorganic support includes silica. In some embodiments, the catalyst includes magnesium oxide. In some embodiments, the magnesium oxide has a surface area in the range of 30 meters-squared/gram (m$^2$/g) to 200 m$^2$/g. In some embodiments, the catalyst includes a first layer of the tungsten oxide impregnated on the inorganic support, a second layer of the tungsten oxide impregnated on the inorganic support, and a layer of the magnesium oxide positioned between the first layer and the second layer. In some embodiments, the catalyst includes a layer of the magnesium oxide disposed on a layer of the tungsten oxide impregnated on the inorganic support. In some embodiments, the volumetric ratio of the magnesium oxide to the tungsten oxide impregnated on the inorganic support is in the range of 1:3 to 3:1. In some embodiments, the system includes an impurities removal bed upstream of the reactor, the impurities removal bed configured to receive the feed stream and remove impurities from the feed stream. In some embodiments, the system includes butadiene extraction unit downstream of the reactor, the butadiene extraction unit configured to separate 1,3-butadiene from the product stream.

In some embodiments, a catalyst for the production of 1,3-butadiene for the production of 1,3-butadiene is provided. The catalyst includes tungsten oxide impregnated on an inorganic support and magnesium oxide. In some embodiments, the catalyst includes a first layer of the tungsten oxide impregnated on the inorganic support, a second layer of the tungsten oxide impregnated on the inorganic support, and a layer of the magnesium oxide positioned between the first layer and the second layer. In some embodiments, the catalyst includes a layer of the magnesium oxide disposed on a layer of the tungsten oxide impregnated on the inorganic support. In some embodiments, the volumetric ratio of magnesium oxide to tungsten oxide impregnated on the inorganic support is in the range of 1:3 to 3:1.

In another embodiment, a method for preparing a catalyst for the conversion of butene to 1,3-butadiene is provided. The method includes calcining a silica support, placing an amount of ammonium metatungstate hydrate solution on the calcined silica support, re-calcining the silica support with the ammonium metatungstate hydrate solution to yield tungsten oxide present on the support, the calcining is performed at first temperature for a first period and second temperature for a second duration. In some embodiments, the method includes drying the silica support having the amount of the ammonium metatungstate hydrate solution. In some embodiments, the first temperature is at least 250° C. and the second period is at least 2 hours, and the second temperature is at least 550° C. and the second period is at least 8 hours. In some embodiments, calcining the silica support includes calcining the silica support at a temperature of at least 200° C. for at least 3 hours and a temperature of at least 575° C. for at least 5 hours before. In some embodiments, the amount of ammonium metatungstate hydrate solution is sufficient to yield 10 weight % (wt %) tungsten oxide on the silica support.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure include processes, systems, and catalysts for the conversion of 2-butene to 1,3-butaidene without the use of steam or, in some embodiments, with a reduced use of steam as compared to prior art processes for the production 1,3-butadiene. In some embodiments, a catalyst includes tungsten oxide ($WO_3$) on an inorganic support, such as silica ($SiO_2$), alumina (e.g., in the form of alumina balls), clay, carbon, or diatomaceous earth. In some embodiments, the catalyst also includes activated magnesium oxide (MgO) and may be referred to as a "dual catalyst" or a "co-catalyst." Embodiments of the catalyst may include various arrangements of the MgO and the $WO_3$-inorganic support including a layer of MgO catalyst positioned between a first layer of WO3-inorganic support catalyst and a second layer of $WO_3$-inorganic support, a layer of MgO catalyst positioned on top of a layer of $WO_3$-inorganic support catalyst, and the MgO catalyst and $WO_3$-inorganic support catalyst mixed in a single layer having both catalysts.

In some embodiments, a process for the production of 1,3-butadiene may include contacting a feed stream of 2-butene with a $WO_3$-inorganic support catalyst or an MgO and $WO_3$-inorganic support catalyst. In some embodiments, the contacting may be performed at a temperature in the range of about 150° C. to about 700° and, in some embodiments, may be performed in the range of about 400° C. to about 550° C. In some embodiments, the feed stream does not include steam and the 1,3-butadiene is produced without steam in the feed stream. As will be appreciated, however, steam may be produced in the oxidative dehydrogenation process, as every butene molecule will generate a molecule of steam for every molecule of 1,3-butadiene produced. In other embodiments, steam diluent may be introduced in a feed stream to aid in heat dissipation and manage temperatures in the catalyst bed. However, in such embodiments that use a steam diluent, the amount of steam may be no more than 50% of the steam used in prior processes for the production of 1,3-butadiene. In some embodiments, the feed stream may also include 1-butene.

In some embodiments, a system for the production of 1, 3-butadiene may include an impurities removal bed, a reactor, and a butadiene extraction unit. In some embodiments, the reactor may be a fixed bed continuous flow reactor. In some embodiments, the reactor may be operated at atmospheric pressure and at a temperature in the range of about 400° C. to about 550° C. In some embodiments, a reactor for producing 1,3-butadiene from 2-butene without the use of steam in accordance with the processes described herein may be a catalyst filled multitubular reactor with a cooling medium on the outside of the tubes.

Processes, Systems, and Catalysts for the Production of 1,3-Butadiene

In some embodiments, a process for the catalytic conversion of 1,3-butadiene from 2-butene includes contacting the 2-butene with a catalyst without steam or with a reduced amount of steam as compared to prior art processes. In some embodiments, steam may be used as a diluent to aid in the dissipation of heat in the catalyst bed and provide for improved management of the temperature rise in the catalyst bed.

In some embodiments, the catalyst includes tungsten oxide ($WO_3$) on an inorganic support, such as silica ($SiO_2$). In some embodiments, the catalyst includes activated magnesium oxide (MgO), and tungsten oxide ($WO_3$) on an inorganic support (the MgO and $WO_3$) catalyst may be referred to as a "dual catalyst" or a "co-catalyst." In some embodiments, the volumetric ratio of MgO catalyst and $WO_3$-inorganic support catalyst may be in the range of about 1:3 to about 3:1. For example, in some embodiments, the volumetric ratio of MgO catalyst and $WO_3$-inorganic support catalyst may be 2:1, 1:1, or 1:2.

In some embodiments, inorganic support for the $WO_3$ may be silica ($SiO_2$). In other embodiments, the catalyst support may be alumina (e.g., in the form of alumina balls), clay, carbon, or diatomaceous earth. In such embodiments, catalysts such as alumina, clay, carbon, or diatomaceous earth may be obtained without any silica impurities so as to reduce or eliminate potential leaching of silica into vapor produced in the reactor and that may foul downstream equipment such as compressor turbine blades.

Embodiments of the disclosure include various arrangements of the MgO and $WO_3$ catalyst. In some embodiments, the catalyst may be held in place in a reactor using an inert material, such as silicon carbide. In some embodiments, the inert material used to hold the catalyst may be Grade 20 silicon carbide (SiC20). In some embodiments, an arrangement may include the layering of the catalyst, the inert material, and an insulating material such as glass wool. In some embodiments, the catalyst arrangement may include a layer of MgO catalyst positioned between a first layer of $WO_3$-inorganic support catalyst and a second layer of $WO_3$-inorganic support. In some embodiments, the catalyst arrangement includes a layer of MgO catalyst positioned on top of a layer of $WO_3$-inorganic support catalyst. In some embodiments, the MgO catalyst and $WO_3$-inorganic support catalyst are mixed in a single layer having both catalysts.

In some embodiments, as noted supra, the inorganic support is silica. In such embodiments, the silica may be prepared by calcining a commercially available silica support. In some embodiments, the calcination may be performed at a temperature of about 200° C. for about 3 hours and then at a temperature of about 575° C. for about 5 hours, with a ramping rate of about 3° C. per minute. In some embodiments, the silica support for the tungsten oxide catalyst may be prepared from a silica support having an average pore diameter of about 10 nm, a pore volume of about 1.00 ml/g, a surface area of about 300 m$^2$/g and a particle size of in the range of about 1.18 mm to about 2.36 mm. In some embodiments, the commercially available silica support may be Q-10 manufactured by Fuji Silysia of Kasugai, Aichi, Japan.

In some embodiments, the tungsten catalyst is prepared by impregnating an inorganic support, such as a silica catalyst support prepared in the manner described in the disclosure. In such embodiments, for example, ammonium metatungstate hydrate with a 99.99% trace metals basis may be used as the tungsten source. In some embodiments, the ammonium metatungstate hydrate may be mixed with DI water and added dropwise to the prepare silica catalyst support and mixed, such as by using a glass rod. The silica catalyst support having the ammonium metatungstate hydrate may be dried in a drying oven and calcined to produce a $WO_3/SiO_2$ catalyst. In some embodiments, silica catalyst support having the ammonium metatungstate hydrate may be dried in a drying oven at a temperature of about 80° C. for a time period of about 8 hours and then calcined at a first temperature of about 250° C. for about 2 hours with a ramping rate of about 1° C. per minute to reach the first temperature and then at a second temperature of about 550° C. for about 8 hours with a ramping rate of about 3° C. per minute until the second temperature is reached.

In some embodiments, the MgO catalyst is prepared from a commercially available MgO. In such embodiments, the MgO may be calcined under air to produce the MgO catalyst. In some embodiments, the MgO may be calcined under air at a rate of about 2° C./minute until a temperature of about 550° C. and then held at about 550° C. for about 150 minutes. In some embodiments, the MgO catalyst may have a surface area in the range of about 30 m$^2$/g to about 200 m$^2$/g. In some embodiments, the MgO catalyst may have a surface area in the range of about 60 m$^2$/g to about 200 m$^2$/g.

In some embodiments, the MgO catalyst may be prepared via co-precipitation using a magnesium salt. In some embodiments, for example, MgO catalyst may be prepared from magnesium nitrate hexahydrate [$Mg(NO_3)_2.6H_2O$]. In such embodiments, the magnesium nitrate hexahydrate may be first mixed with DI water and the magnesium nitrate hexahydrate solution added dropwise to a container of DI water. The mixture may be stirred at about 600 rpm while ammonium hydroxide is added simultaneously to the mixture, and then stirred for about an hour. The mixture may then be centrifuged and washed with DI water. The solid from the solution may be collected and dried in a drying oven at a temperature of about 80° C. and calcined under air at a rate of about 2° C./minute until a temperature of about 550° C. and then held at about 550° C. for about 150 minutes.

In some embodiments, the MgO catalyst may be produced by hydrating commercially available MgO by converting it to $Mg(OH)_2$ and then calcining it under air to convert the $Mg(OH)_2$ back to MgO.

In some embodiments, a system for catalyst conversion of 1,3-butadiene from 2-butene using the catalysts described in the disclosure may include a fixed bed continuous flow reactor. In some embodiments, the reactor may be operated at atmospheric pressure. In some embodiments, the reactor may be operated at a temperature in the range of about 150° C. to about 700° and, in some embodiments, may be performed in the range of about 400° C. to about 550° C. In some embodiments, a reactor for producing 1,3-butadiene from 2-butene without the use of steam in accordance with the processes described herein may be a catalyst filled multitubular reactor with a cooling medium on the outside of the tubes. As will be appreciated, steam may be produced during the oxidative dehydrogenation reaction, as every 2-butene molecule will generate a molecule of steam for every molecule of 1,3-butadiene produced.

Figure 1:
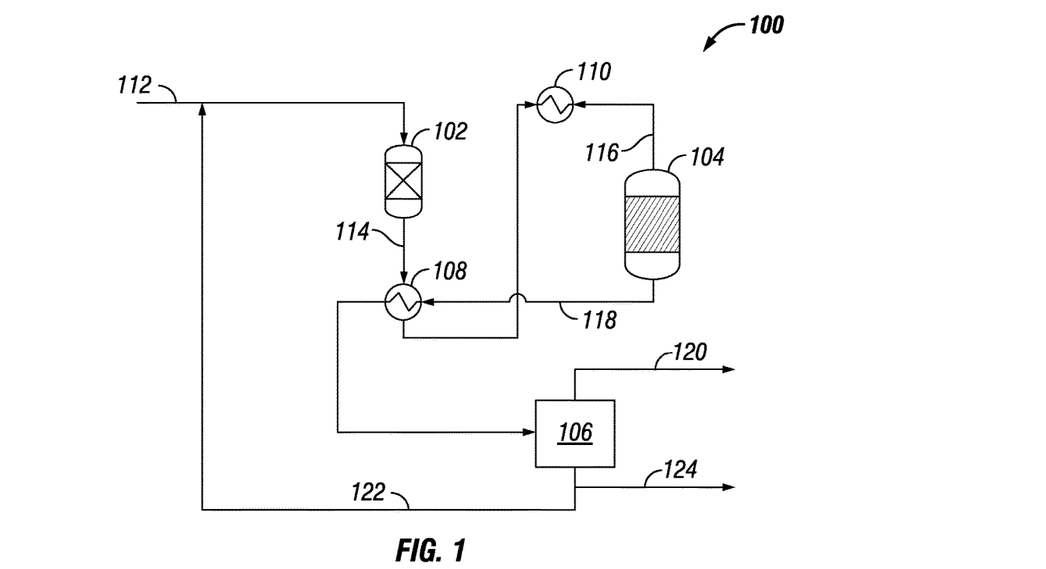
FIG. 1 is a schematic diagram of a system for the conversion of 2-butene to 1,3-butadiene in accordance with an embodiment of the disclosure.

FIG. 1 depicts a system 100 for the conversion of 2-butene to 1,3-butadiene in accordance with an embodiment of the disclosure. As shown in FIG. 1, the system 100 may include an impurities removal bed 102, a reactor 104, and a butadiene extraction unit 106. The system 100 may also include heat exchanger 108 and 110. The system 100 may receive a butene feed stream 112 having 2-butene. In some embodiments, the feed stream 112 includes cis- and trans-2-butene. In some embodiments, the feed stream 112 may include air or air may be provided in a separate stream.

The feed stream 112 may be provided to the impurities removal bed 100 to remove impurities from the feed stream 112. In some embodiments, the purified feed stream 114 from the impurities removal bed 102 may be provided to the heat exchanger 108 to be heated using the output stream from the reactor 104. In some embodiments, the purified feed stream 114 may be provided to a second heat exchanger 110 to produce a purified and heated feed stream 116. The purified and heated feed stream 116 may be provided to the reactor 104 for conversion of 2-butene in the feed stream 116 to 1,3-butadiene using the techniques described in the disclosure.

The output stream 118 from the reactor 104 may include 1,3-butadiene converted from the 2-butene, as well as other reaction products and unreacted feed components. The output stream 118 may be heated by the exothermic conversion reaction and may be provided to the heat exchanger 108 to provide heat to and increase the temperature of the purified feed stream 114 and cool the output stream 118. The cooled output stream may be provided to the butadiene extraction unit 106 for extraction of the 1,3-butadiene. Accordingly, the 1-3-butadiene extraction unit may provide a product stream 120 of 1,3-butadiene and a butene stream 122. In some embodiments, the butadiene extraction unit 106 may include oil adsorption and extraction separation to purify the 1-3-butadiene from byproducts. In some embodiments, a portion 124 of the butene stream 122 may be sent to a purge. In some embodiments, as shown in FIG. 1, some or all of the butene stream 122 may be recycled to the feed stream 112.

It should be appreciated that, in some embodiments, the system 100 may include other components. For example, in some embodiments the system may include an acetylenes and aldehydes removal (AAR) bed downstream of the reactor 106. Alternatively, in some embodiments, the system 100 may include a KLP-60 (DOW-UOP) catalyst reactor to selectively hydrogenate acetylenics and reduce oxygenates to water and alkanes. As will be appreciated, in such embodiments a promoted palladium (Pd) based catalyst may provide improved reduction of oxygenates to water but may be less selective in taking C4 acetylenics to butenes and 1-3, butadiene as compared to KLP-60.

EXAMPLES

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

Examples of the preparation of various catalysts which are used separately or in combination for the catalytic conversion of 2-butene to 1,3-butadiene are described below.

Example Silica Blank

Silica blanks were prepared by placing a desired amount of Q-10 silica catalyst support manufactured by Fuji Silysia of Kasugai, Aichi, Japan, was placed in a ceramic plate. The Q-10 sample was then calcined at 200° C. for about three hours and then at 575° C. for about five hours, with a ramping rate of 3° C. per minute. The properties of the Q-10 silica catalyst support are shown in Table 1:

TABLE 1

Properties of Q-10 Silica Catalyst Support

| | Average Pore Diameter (millimeters (mm)) | Pore Volume (milliliters/grams (ml/g)) | Surface Area (meters-squared/grams ($m^2/g$)) | Particle Size (mm) |
|---|---|---|---|---|
| Q-10 | 10 | 1.00 | 300 | 1.18-2.36 |

Figure 2:
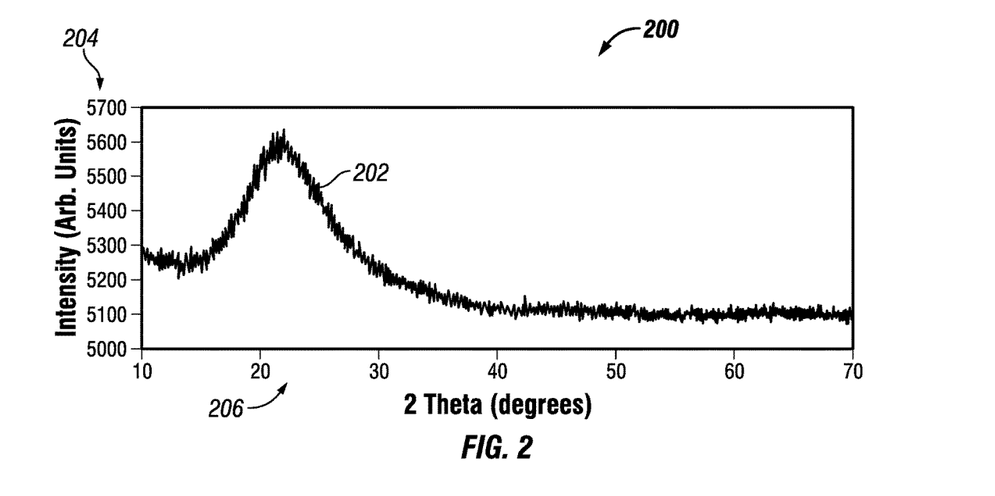
FIG. 2 is a plot of x-ray diffraction (XRD) patterns of a prepared silica blank in accordance with an embodiment of the disclosure.

FIG. 2 is a plot 200 of x-ray diffraction (XRD) patterns 202 of the prepared silica blank. FIG. 2 depicts the intensity (in arbitrary units) on the y-axis 204 and 2 theta (in degrees) on the x-axis 206. As shown in FIG. 2, the broad peak in 2 theta from 15° to 30° is due to the silica support.

The Brunauer-Emmett-Teller (BET) theory was used to determine the surface area and pore volume of the silica blank and the prepare catalysts described supra. Table 2 depicts the BET results for the surface area and volume of the prepared silica blank:

TABLE 2

BET Surface Area and Pore Volume for Silica Blank

| Sample | BET Surface Area ($m^2/g$) | Pore Volume ($cm^3/g$) |
|---|---|---|
| Silica blank | 304.41 | 1.13 |

Example Preparation of Silica Support Impregnated with a Tungsten Precursor 2 grams of the silica blank prepared in the manner described above were placed in an 80 ml beaker. 0.235 g of ammonium metatungstate hydrate having 99.99% trace metals was weighted out and mixed with 2 ml of deionized (DI) water. The ammonium metatungstate hydrate and DI water solution was added dropwise to the silica blank. In a typical example, 5 drops of the ammonium metatungstate hydrate and DI water solution were placed on the silica blank. A glass rod was used to thoroughly mix the support. Next, the catalyst was placed in a drying oven overnight at about 80° C. The dried catalyst was then calcined at about 250° C. for about 2 hours and at about 550° C. for about 8 hours, with ramping rate of about 1° C. per minute until the first temperature was reached and about 3° C. until the second temperature was reached. The resulting catalyst had about 10 weight (wt) % tungsten loaded on the silica blank support.

Figure 3:
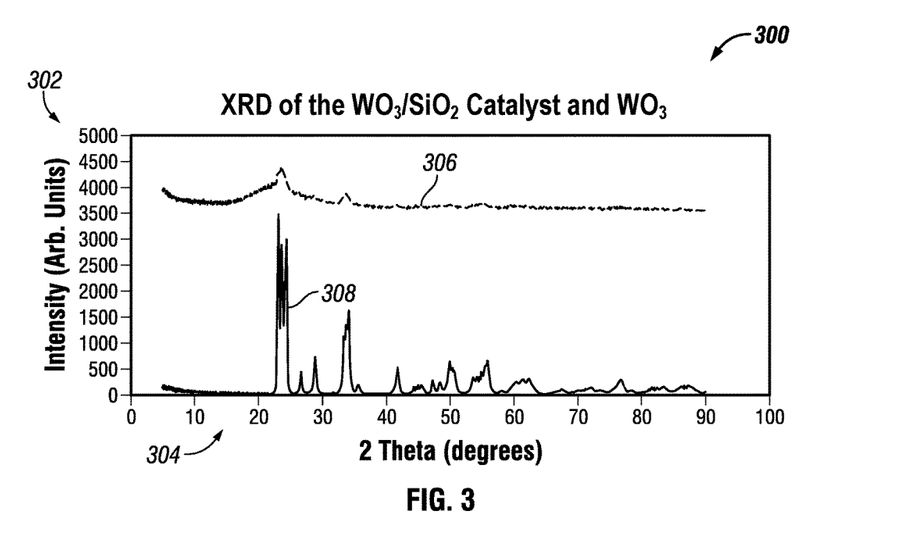
FIG. 3 is a plot of x-ray diffraction (XRD) patterns for a prepared $WO_3/SiO_2$ catalyst and $WO_3$ in accordance with an embodiment of the disclosure.

FIG. 3 is a plot 300 of x-ray diffraction (XRD) patterns for the prepared $WO_3$/Si catalyst and the $WO_3$. FIG. 3 depicts the intensity (in arbitrary units) on the y-axis 302 and 2 theta (in degrees) on the x-axis 304. The XRD pattern for the $WO_3$/Si catalyst is depicted by line 306, and the XRD pattern for $WO_3$ (from the ammonium metatungstate hydrate bottle after calcination at about 550° C. for about 2 hours at a ramping rate of about 1° C.). Thus, the pattern shown by line 308 does not contain any silica, only calcined ammonium metatungstate.

The BET theory was used to determine the surface area and pore volume of the prepared $WO_3$/Si catalyst. Table 2 depicts the BET results for the surface area and volume of the prepared $WO_3$/Si catalyst:

TABLE 3

BET Surface Area and Pore Volume for $WO_3$/Si catalyst

| Sample | BET Surface Area ($m^2/g$) | Pore Volume ($cm^3/g$) |
|---|---|---|
| $WO_3$/Si catalyst | 274.35 | 0.81 |

As compared to the silica blank, the surface area and pore volume is slightly reduced after the tungsten is loaded onto the support.

Example Preparation of MgO Commercial Catalyst

Commercial MgO was obtained from Sigma-Aldrich. The MgO was Lot#MKBQ2256V with ≥99% trace metals basis obtained from Sigma-Aldrich Corporation of St. Louis, Mo., USA. 4 g of the commercial MgO was calcined under air at a rate of about 2° C./minute until it reached about 550° C. The temperature was held at about 550° C. for about 150 minutes. Following calcination, the commercial MgO was allowed to slowly cool to room temperature inside the calcination oven.

Figure 4:
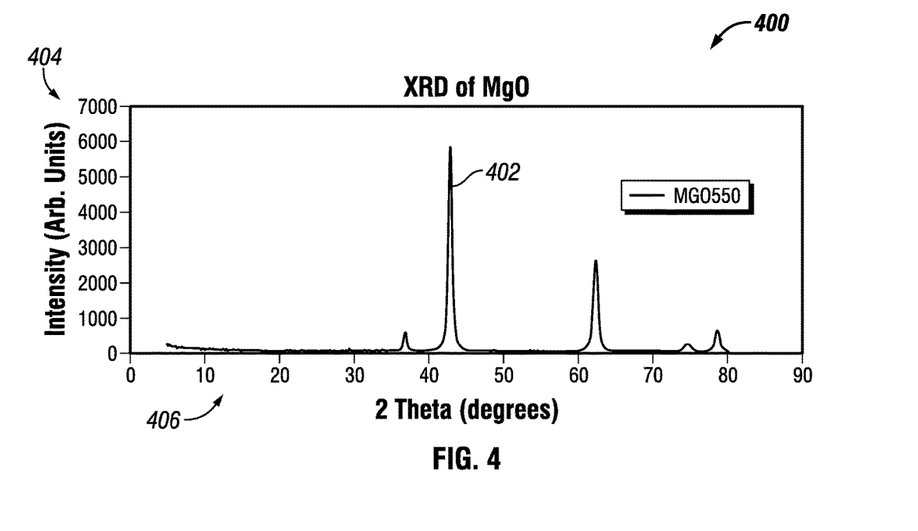
FIG. 4 is a plot of x-ray diffraction (XRD) patterns of an MgO catalyst prepared from commercially available MgO in accordance with an embodiment of the disclosure.

FIG. 4 is a plot 400 of x-ray diffraction (XRD) patterns 402 of the MgO catalyst prepared from the commercially available MgO FIG. 4 depicts the intensity (in arbitrary units) on the y-axis 404 and 2 theta (in degrees) on the x-axis 406. As shown in FIG. 4, the diffraction peaks corresponding to crystalline MgO can be observed at 2 theta values of 37.0°, 43.0°, 62.4°, 74.8°, and 78.7°. At calcination temperatures greater than about 400° C., the $Mg(OH)_2$ is mostly or completely converted to MgO. Thus, the greater the calcination temperature, the calcination time, or both, the sharper the diffraction peaks (that is, the greater the intensity).

BET theory was used to determine the surface area and pore volume of the MgO catalyst prepared from the commercially available MgO. Barrett-Joyner-Halenda (BJH) analysis was also used to estimate the surface area of the prepared MgO catalyst. Table 4 depicts the BET results for the surface area and pore volume and the BJH results for pore volume for the prepared MgO catalyst:

TABLE 4

BET Surface Area, BJH Surface Area, and Pore Volume for MgO catalyst

| Sample | BET Surface Area ($m^2/g$) | BJH Surface Area ($m^2/g$) | Pore Volume ($cm^3/g$) |
|---|---|---|---|
| MgO catalyst | 60.585 | 74.67 | 0.289 |

Example Preparation of MgO Using Co-precipitation

MgO was also prepared using a co-precipitation technique as an alternative to prepare the MgO catalyst. 25.64 g of magnesium nitrate hexahydrate ([MgO(NO$_3$).H$_2$O]) was mixed with 100 ml of DI water in a beaker. In another beaker, 100 ml of DI water was added. The solution in the first beaker was then added dropwise using a pipette to the second beaker containing only DI water. A magnetic stirrer was placed inside the beaker and set to stir at about 600 revolutions-per-minute (600 rpm). Ammonium hydroxide was simultaneously added dropwise to the solution while the solution was being stirred to maintain the pH of the solution in the range of about 11 to about 12. After adding the magnesium nitrate hexahydrate, the solution was left to stir for an hour at about 600 rpm. The solution was then centrifuged and washed using DI water for about 4 or 5 times. A white solid was collected and dried in a drying oven overnight at 80° C. The dried solid was calcined under air at a rate of about 2° C./minute until it reached about 550° C. The temperature was held at about 550° C. for about 150 minutes. Following calcination, the co-precipitated MgO was allowed to slowly cool to room temperature inside the calcination oven.

Example Preparation of MgO by Hydrating Commercial MgO

MgO was also prepared by hydrating commercially available MgO as an alternative to prepare the MgO catalyst and enhance the properties of the MgO. The hydration was performed by converting the commercially available MgO to Mg(OH)$_2$ and then calcining the Mg(OH)$_2$ under air to convert it back to MgO.

The commercially available MgO was Lot# MKBQ2256V with ≥99% trace metals basis obtained from Sigma-Aldrich Corporation of St. Louis, Mo., USA. About 24.00 g of the commercially available MgO was weighed out and added to a 500 ml round-bottom flask. About 300 ml of water was added to the MgO, and the solution was vigorously shaken for about 5 minutes. The round-bottom flask was then connected to rotary evaporator apparatus which was run at about 171 rpm in a water bath which was maintained at a temperature in the range of about 80° C. to about 95° C. under a vacuum of about 295 mbar, while maintaining a coolant at about −14.4° C. (6° F.). All the water was evaporated for a time period of up to about 4 hours. After evaporating all of the water, the round-bottom flask was placed in a drying oven overnight, which operated between about 80° C. to about 100° C. A solid was collected and calcined under air at a rate of about 2° C./minute until it reached about 550° C. The temperature was held at about 550° C. for about 150 minutes. Following calcination, the hydrated MgO was allowed to slowly cool to room temperature inside the calcination oven.

Catalyst Testing

The prepared catalysts were tested for their activity and selectivity in a fixed bed continuous flow reactor at atmospheric pressure. The fixed bed continuous flow reactor had an inner diameter of 0.25 inches and was obtained from Autoclave Engineers Ltd. A 2 ml sample of each catalyst was loaded into the reactor for each test. The bottom of the reactor was packed with 14 g of Grade 20 silicon carbide (SiC20), as shown in Table 5. The silicon carbide was used to hold the catalyst in place in the isothermal zone and does not contribute to the reaction. Different loading configurations and catalyst amounts were tested. The different loading configurations and catalyst amount combinations may be referred to as Schemes A-E and Scheme MgO and are shown in Table 5:

TABLE 5

| | Loading Configurations and Catalyst Amounts | | | | | |
|---|---|---|---|---|---|---|
| Scheme | A | B | C | D | E | (MgO) |
| Layering/Mixed (Top to bottom configuration) | Glass Wool | Glass Wool | Glass Wool | Glass Wool | Glass Wool | Glass Wool |
| | WO3/SiO2 (1 ml) | WO3/SiO2 (2 ml) | MgO (1 ml) | MgO (1 ml) mixed with WO3/SiO2 | WO3/SiO2 (1 ml) | MgO (2 ml) |
| | MgO (1 ml) | Glass Wool | WO3/SiO2 (2 ml) | | MgO (2 ml) | Glass Wool |
| | WO3/SiO2 (1 ml) | SiC20 | Glass Wool | | WO3/SiO2 (1 ml) | SiC20 |
| | Glass Wool | Glass Wool | SiC20 | Glass Wool | Glass Wool | Glass Wool |
| | SiC20 | N/A | Glass Wool | SiC20 | SiC20 | N/A |
| | Glass Wool | N/A | N/A | Glass Wool | Glass Wool | N/A |

The tested catalysts were pretreated and activated under about 25 standard cubic centimeter per minute (sccm) at about 550° C. for about 60 minutes. The ramping time to 550° C. was about 90 minutes. A gas hourly space velocity (GHSV) of 900 inverse hours (h$^{-1}$) was maintained using a 2-butene feed at about 5 ml/min with air as an oxidant and diluent at about 25 ml/min. The 2-butene feed to the reactor includes a weight ratio of cis-2-butene to trans-2-butene of 50:50. The quantitative analysis of the reaction products was performed online using an Agilent GC-7890B gas chromatograph (GC) with an HP-Al/KCL (50 m×0.53 mm×15 microns) column, manufactured by Agilent Technologies of Santa Clara, Calif. The GC was equipped with a flame ionization detector (FID).

The conversion of 2-butene was determined using Equation 1:

$$X_i = \frac{\dot{n}_{i,in} - \dot{n}_{i,out}}{\dot{n}_{i,in}} = 1 - \frac{\dot{n}_{i,out}}{\dot{n}_{i,in}} \quad (1)$$

Where X is the conversion and $\dot{n}$ is the number of moles of 2-butene (including both cis- and trans-2-butene).

The selectivity was determined using Equation 2:

$$\text{Selectivity} = \frac{\text{Yield of Product}}{\text{Conversion}} \times 100 \quad (2)$$

Scheme A from Table 5 was run at three temperatures of about 450° C., about 500° C., and about 550° C. for about 3.5 hours at each temperature consecutively for a total of about 12 hours. Table 6A shows the reaction temperature, time on stream (TOS in hours:minutes:seconds (hr:min:s)), yields (in mole %) for each product, and Table 6B shows reaction temperature, TOS, and the conversion rate, and the 1,3-butadience selectivity for each temperature:

TABLE 6A

Reaction Temperature, Time on stream (TOS), and product yields for Scheme A

| Temp (° C.) | TOS (hr:min:s) | Trans-2-butene | 1-Butene | IsoBu-tylene | Cis-2-butene | 1,3-BD |
|---|---|---|---|---|---|---|
| 450 | 0:38:22 | 38.3181 | 25.3496 | 0.2584 | 28.0981 | 7.7485 |
| 450 | 1:25:18 | 38.0584 | 25.0404 | 0.1827 | 28.0283 | 8.4587 |
| 450 | 2:12:14 | 37.9521 | 24.6634 | 0.1579 | 28.0713 | 8.9185 |
| 450 | 2:59:12 | 37.9512 | 24.4936 | 0.1462 | 27.9235 | 9.1139 |
| 477.8 | 3:46:10 | 36.9916 | 24.4655 | 0.1599 | 27.2699 | 10.5852 |
| 500 | 4:33:07 | 33.6011 | 24.6383 | 0.2651 | 25.1875 | 15.5428 |
| 500 | 5:20:02 | 32.9176 | 24.4389 | 0.2587 | 24.8977 | 16.5992 |
| 500 | 6:06:58 | 32.8852 | 24.4844 | 0.2382 | 24.699 | 16.9742 |
| 500 | 6:53:56 | 32.7447 | 24.3043 | 0.2275 | 24.5618 | 17.4584 |
| 518 | 7:40:53 | 32.164 | 24.0704 | 0.2223 | 24.1511 | 18.3839 |
| 550 | 8:27:49 | 28.1968 | 22.7696 | 0.279 | 21.5375 | 24.809 |
| 550 | 9:14:47 | 27.7022 | 22.3565 | 0.2496 | 21.0096 | 26.1412 |
| 550 | 10:01:41 | 27.9266 | 22.1623 | 0.2253 | 21.1183 | 25.8547 |
| 550 | 10:48:39 | 28.2061 | 21.9843 | 0.2092 | 21.5527 | 25.1516 |
| 533 | 11:35:36 | 28.6295 | 21.8853 | 0.1985 | 21.8109 | 24.5762 |

TABLE 6B

Conversion Rate and 1,3-BD Selectivity for Scheme A

| Temp (° C.) | TOS (hr:min:s) | Conversion | 1,3-BD Selectivity |
|---|---|---|---|
| 450 | 0:38:22 | 33.5838 | 23.07213597 |
| 450 | 1:25:18 | 33.9133 | 24.94213185 |
| 450 | 2:12:14 | 33.9766 | 26.24894781 |
| 450 | 2:59:12 | 34.1253 | 26.70716448 |
| 477.8 | 3:46:10 | 35.7385 | 29.61847867 |
| 500 | 4:33:07 | 41.2114 | 37.71480707 |
| 500 | 5:20:02 | 42.1847 | 39.34886345 |
| 500 | 6:06:58 | 42.4158 | 40.01857798 |
| 500 | 6:53:56 | 42.6935 | 40.89240751 |
| 518 | 7:40:53 | 43.6849 | 42.08296231 |
| 550 | 8:27:49 | 50.2657 | 49.35572368 |
| 550 | 9:14:47 | 51.2882 | 50.96922879 |
| 550 | 10:01:41 | 50.9551 | 50.74016144 |
| 550 | 10:48:39 | 50.2412 | 50.06170235 |
| 533 | 11:35:36 | 49.5596 | 49.58918151 |

Table 7A shows, for each reaction temperature, the average yields for each product, and Table 7B shows, for each reaction temperature, the average conversion rate, and the average butadiene selectivity, based on the data from Tables 6A and 6B:

TABLE 7A

Average product yields for Scheme A

| # of data points, n= | Temp (° C.) | Trans-2-butene | 1-Butene | IsoButylene | Cis-2-butene | 1,3-BD |
|---|---|---|---|---|---|---|
| 4 | 450 | 38.06995 | 24.88675 | 0.1863 | 28.0303 | 8.5599 |
| 4 | 500 | 33.03715 | 24.46648 | 0.247375 | 24.8365 | 16.64365 |
| 4 | 550 | 28.00793 | 22.31818 | 0.240775 | 21.30453 | 25.48913 |

TABLE 7B

Average Conversion Rate and 1,3-BD Selectivity for Scheme A

| # of data points, n= | Temp (° C.) | Conversion | 1,3-BD Selectivity |
|---|---|---|---|
| 4 | 450 | 33.89975 | 25.2426 |
| 4 | 500 | 42.12635 | 39.49366 |
| 4 | 550 | 50.68755 | 50.2817 |

Upon running the test of Scheme A, it was observed that a period of time elapses after the 2-butene feed stream is run before the 1,3-butadiene yield begins to increase, especially at the lower testing temperatures. This period of time is more pronounced with the catalyst that includes MgO. To speed up the production of 1,3-butdiene, the reaction temperature may be increased to about 550° C. and then reduced.

It was also observed that running the reaction at 550° C. for an extended period time deactivates the catalyst. The optimal reaction temperature was thus determined to be in the range of about 450° C. to about 500° C. for the catalyst system of Scheme A.

The addition of more MgO (in the ratio of about 1:1, about 2:1, and about 3:1 of MgO to $WO_3/SiO_2$) may increase the stability and slowdown the deactivation of the catalyst.

In Scheme B from Table 5, MgO was removed from the catalyst system and the $WO_3/SiO_2$ was tested individually by loading about 2 ml of $WO_3/SiO_2$ in the reactor. Scheme B from Table 5 was run at a temperature of about 500° C. Table 8A shows the reaction temperature, time on stream (TOS), yields (in mole %) for each product, and Table 8B shows reaction temperature, TOS, and the conversion rate, and the 1,3-butadience selectivity:

TABLE 8A

Reaction Temperature, Time on stream (TOS), and product yields for Scheme B

| Temp (° C.) | TOS (hr:min:s) | Trans-2-butene | 1-Butene | IsoBu-tylene | Cis-2-butene | 1,3-BD |
|---|---|---|---|---|---|---|
| 500 | 0:36:25 | 34.087 | 21.923 | 0.212 | 23.509 | 16.802 |
| 500 | 1:23:21 | 38.261 | 22.637 | Less than 0.2 | 26.734 | 12.368 |
| 500 | 2:10:17 | 38.407 | 22.872 | than 0.2 | 27.457 | 11.264 |
| 500 | 2:57:17 | 38.699 | 23.021 | | 27.704 | 10.576 |
| 500 | 3:44:15 | 39.005 | 23.129 | | 27.855 | 10.012 |
| 500 | 4:31:12 | 39.038 | 23.115 | | 28.26 | 9.588 |
| 500 | 5:18:11 | 39.259 | 23.188 | | 28.346 | 9.207 |

TABLE 8B

Average Conversion Rate and 1,3-BD Selectivity for Scheme B

| Temp (° C.) | TOS (hr:min:s) | Conversion | 1,3-BD Selectivity |
|---|---|---|---|
| 500 | 0:36:25 | 42.405 | 39.623 |
| 500 | 1:23:21 | 35.005 | 35.332 |
| 500 | 2:10:17 | 34.137 | 32.998 |
| 500 | 2:57:17 | 33.597 | 31.479 |
| 500 | 3:44:15 | 33.14 | 30.21 |
| 500 | 4:31:12 | 32.702 | 29.318 |
| 500 | 5:18:11 | 32.396 | 28.421 |

As shown in Tables 8A and 8B, the conversion, 1,3-butadiene selectivity, and the 1,3-butadiene yield decrease at a faster rate than the catalyst system of Scheme A having the dual catalysts. The MgO catalyst appeared to stabilize the reaction and reduce catalyst deactivation.

$WO_3/SiO_2$ was removed from the catalyst system and MgO was tested individually to observe the contribution of MgO to the oxidative dehydrogenation. About 2 ml of MgO was loaded in the reactor, and the individual MgO was run at three temperatures of about 450° C., about 500° C., and about 550° C. Table 9A shows the reaction temperature, time on stream (TOS), yields (in mole %) for each product, and Table 9B shows reaction temperature, TOS, and the conversion rate, and the 1,3-butadience selectivity:

TABLE 9A

Reaction Temperature, Time on stream (TOS), and product yields for MgO individually

| Temp (° C.) | TOS (hrs:mins:sec) | Methane | Ethane | Trans-2-butene | 1-Butene | IsoButylene | Cis-2-butene | 1,3-BD |
|---|---|---|---|---|---|---|---|---|
| 400 | 0:46:59 | 0 | 0 | 50.849 | 1.703 | 0 | 46.586 | 0.862 |
| 400 | 1:34:02 | 0 | 0 | 50.731 | 1.290 | 0 | 47.156 | 0.823 |
| 400 | 2:21:02 | 0 | 0 | 50.521 | 1.177 | 0 | 47.484 | 0.817 |
| 400 | 3:08:02 | 0 | 0 | 50.696 | 1.136 | 0 | 47.359 | 0.809 |
| 400 | 3:55:05 | 0 | 0 | 50.490 | 1.090 | 0 | 47.631 | 0.790 |
| 400 | 4:42:08 | 0 | 0 | 50.485 | 1.096 | 0 | 47.630 | 0.789 |
| 430 | 5:29:04 | 0 | 0 | 49.634 | 1.880 | 0 | 46.667 | 1.819 |
| 450 | 6:16:05 | 0 | 0 | 48.947 | 2.747 | 0 | 45.368 | 2.939 |
| 450 | 7:03:02 | 0 | 0 | 48.970 | 2.773 | 0 | 45.325 | 2.933 |
| 450 | 7:50:00 | 0 | 0 | 49.404 | 2.815 | 0 | 44.896 | 2.884 |
| 450 | 8:36:57 | 0 | 0 | 50.285 | 2.967 | 0 | 43.889 | 2.859 |
| 450 | 9:23:56 | 0 | 0 | 50.127 | 3.119 | 0 | 43.906 | 2.849 |
| 450 | 10:10:53 | 0 | 0 | 49.868 | 3.320 | 0 | 43.976 | 2.836 |
| 500 | 10:57:50 | 0 | 0 | 47.734 | 7.262 | 0 | 39.889 | 5.115 |
| 500 | 11:44:47 | 0.130 | 0.141 | 46.506 | 7.009 | 0 | 39.433 | 6.782 |
| 500 | 12:31:47 | 0.128 | 0.135 | 47.097 | 5.645 | 0 | 40.067 | 6.929 |
| 500 | 13:18:46 | 0.126 | 0.132 | 47.186 | 5.219 | 0 | 40.307 | 7.031 |
| 500 | 14:05:42 | 0.129 | 0.132 | 47.420 | 5.086 | 0 | 40.084 | 7.149 |
| 500 | 14:52:42 | 0.130 | 0.130 | 47.265 | 5.123 | 0 | 40.139 | 7.214 |
| 500 | 15:39:37 | 0.130 | 0.135 | 47.175 | 5.166 | 0 | 40.160 | 7.235 |

TABLE 9B

Average Conversion Rate and 1,3-BD Selectivity for MgO individually

| Temp (° C.) | TOS (hrs:mins:sec) | Conversion | 1,3-BD Selectivity |
|---|---|---|---|
| 400 | 0:46:59 | 2.565 | 33.608 |
| 400 | 1:34:02 | 2.113 | 38.934 |
| 400 | 2:21:02 | 1.995 | 40.979 |
| 400 | 3:08:02 | 1.945 | 41.573 |
| 400 | 3:55:05 | 1.880 | 42.036 |
| 400 | 4:42:08 | 1.885 | 41.851 |
| 430 | 5:29:04 | 3.699 | 49.177 |
| 450 | 6:16:05 | 5.685 | 51.686 |
| 450 | 7:03:02 | 5.706 | 51.402 |
| 450 | 7:50:00 | 5.699 | 50.604 |
| 450 | 8:36:57 | 5.826 | 49.070 |
| 450 | 9:23:56 | 5.967 | 47.735 |
| 450 | 10:10:53 | 6.156 | 46.071 |
| 500 | 10:57:50 | 12.377 | 41.329 |
| 500 | 11:44:47 | 14.061 | 48.228 |
| 500 | 12:31:47 | 12.836 | 53.980 |
| 500 | 13:18:46 | 12.507 | 56.214 |
| 500 | 14:05:42 | 12.496 | 57.212 |
| 500 | 14:52:42 | 12.596 | 57.268 |
| 500 | 15:39:37 | 12.666 | 57.120 |

As shown in Tables 9A and 9B, the contribution of MgO does not become significant until the reaction temperature reaches about 500° C.; however, MgO also deactivates at that temperature. The catalyst removed from the reactor after the testing of MgO individually was observed to be dark black and showed coke. The other catalysts removed from the other experiments of Scheme A and Scheme B were observed to be light to dark grey.

In Scheme C from Table 5, the MgO was placed on top of the $WO_3/SiO_2$ (as opposed to the MgO sandwiched between two layers of $WO_3/SiO_2$ as in Scheme A). As shown in Table 5, about 2 ml of $WO_3/SiO_2$ and 1 ml of MgO were loaded in the reactor. The rest of the layers in Scheme C were identical to Scheme A. Scheme C from Table 5 was run at a temperature of about 500° C. for about 5 hours. Table 10A shows the reaction temperature, time on stream (TOS), yields (in mole %) for each product, and Table 10B shows reaction temperature, TOS, and the conversion rate, and the 1,3-butadience selectivity:

TABLE 10A

Reaction Temperature, Time on stream (TOS), and product yields for Scheme C

| Temp (° C.) | TOS (hrs:min:s) | Trans-2-butene | 1-Butene | IsoBu-tylene | Cis-2-butene | 1,3-BD |
|---|---|---|---|---|---|---|
| 500 | 0:50:00 | 33.392 | 18.515 | 0 | 24.588 | 22.983 |
| 500 | 1:36:59 | 33.948 | 18.152 | 0 | 25.046 | 22.486 |
| 500 | 2:23:58 | 34.523 | 17.648 | 0 | 25.36 | 22.099 |
| 500 | 3:10:57 | 35.013 | 17.335 | 0 | 25.661 | 21.629 |
| 500 | 3:57:54 | 36.314 | 20.676 | 0 | 26.399 | 19.368 |

TABLE 10B

Average Conversion Rate and 1,3-BD Selectivity for Scheme C

| Temp (° C.) | TOS (hrs:min:s) | Conversion | 1,3-BD Selectivity |
|---|---|---|---|
| 500 | 0:50:00 | 42.02 | 54.695 |
| 500 | 1:36:59 | 41.006 | 54.836 |
| 500 | 2:23:58 | 40.117 | 55.086 |
| 500 | 3:10:57 | 39.326 | 54.998 |
| 500 | 3:57:54 | 37.29 | 51.939 |

Table 11A shows the average yields for each product, and Table 11B shows the average conversion rate, and the average butadiene selectivity, based on the data points at the reaction temperature, based on the data from Tables 10A and 10B:

TABLE 11A

Average product yields for Scheme C

| # of data points, n= | Temp (° C.) | Trans-2-butene | 1-Butene | IsoBu-tylene | Cis-2-butene | 1,3-BD |
|---|---|---|---|---|---|---|
| 5 | 500 | 34.638 | 18.465 | 0 | 25.411 | 21.113 |

TABLE 11B

Average Conversion Rate and 1,3-BD Selectivity for Scheme C

| # of data points, n= | Temp (° C.) | Conversion | 1,3-BD Selectivity |
|---|---|---|---|
| 5 | 500 | 39.952 | 52.702 |

As shown in Tables 10B and 11B, placing the MgO catalyst on top of the WO$_3$/SiO$_2$ catalyst increased the 1,3-butadiene selectivity at 500° C. while not significantly changing the conversion as compared to Scheme A. However, the catalyst in Scheme C deactivated faster than the catalyst used in Scheme A; however, the rate of deactivation was slower than the catalyst used in Scheme B (the catalyst without MgO).

In Scheme D from Table 5, the MgO was physically mixed with the WO$_3$/SiO$_2$ catalyst. Scheme D from Table 5 was run at a temperature of about 450° C. for about 5 hours. Table 12A shows the reaction temperature, time on stream (TOS), yields (in mole %) for each product, and Table 12B shows reaction temperature, TOS, and the conversion rate, and the 1,3-butadience selectivity:

TABLE 12A

Reaction Temperature, Time on stream (TOS), and product yields for Scheme D

| Temp (° C.) | TOS (hrs:mins:s) | Trans-2-butene | 1-Butene | IsoBu-tylene | Cis-2-butene | 1,3-Buta-diene |
|---|---|---|---|---|---|---|
| 450 | 0:45:08 | 38.0074 | 25.2848 | 0.2663 | 27.8047 | 8.3605 |
| 450 | 1:31:21 | 37.8649 | 25.323 | 0.2367 | 27.8688 | 8.434 |
| 450 | 2:17:42 | 37.9398 | 25.2475 | 0.213 | 27.9252 | 8.2049 |
| 450 | 3:04:00 | 38.0492 | 25.2778 | 0.1976 | 27.8681 | 8.1454 |
| 450 | 3:50:16 | 38.1226 | 25.1738 | 0.1821 | 27.9656 | 8.094 |
| 450 | 4:36:30 | 38.1136 | 25.1528 | 0.1759 | 27.9749 | 8.1011 |

TABLE 12B

Reaction Temperature, Time on stream (TOS), and product yields for Scheme D

| Temp (° C.) | TOS (hrs:mins:s) | Conversion | 1,3-BD Selectivity |
|---|---|---|---|
| 450 | 0:45:08 | 34.1879 | 24.455 |
| 450 | 1:31:21 | 34.2663 | 26.139 |
| 450 | 2:17:42 | 34.135 | 24.037 |
| 450 | 3:04:00 | 34.0827 | 23.899 |
| 450 | 3:50:16 | 33.9118 | 23.868 |
| 450 | 4:36:30 | 33.9115 | 23.889 |

Table 13A shows the average yields for each product, and Table 13B shows the average conversion rate, and the average butadiene selectivity, based on the data points at the reaction temperature, based on the data from Tables 12A and 12B:

TABLE 13A

Average product yields for Scheme D

| # of data points, n= | Temp (° C.) | Trans-2-butene | 1-Butene | IsoBu-tylene | Cis-2-butene | 1,3-BD |
|---|---|---|---|---|---|---|
| 6 | 450 | 38.016 | 25.243 | 0.212 | 27.901 | 8.223 |

TABLE 13B

Average Conversion Rate and 1,3-BD Selectivity for Scheme D

| # of data points, n= | Temp (° C.) | Conversion | 1,3-BD Selectivity |
|---|---|---|---|
| 6 | 450 | 34.083 | 24.128 |

As shown in Tables 12A, 12B, 13A, and 13C, the performance of the catalysts in Scheme D was similar to that catalyst system in Scheme A. In both schemes, testing was performed at about 450° C. and the amount of catalyst was unchanged; the only difference was the layering of the catalyst.

As shown above, of the layering schemes tested, Schemes A and D were the most stable and produced optimal amounts of 1,3-butadiene without increasing the rate of catalyst deactivation.

In Scheme E from Table 5, the same layering from Scheme A was used but the amount of the MgO catalyst was doubled. About 2 ml of the MgO catalyst and about 2 ml in the WO$_3$/SiO$_2$ catalyst was loaded in the reactor. Scheme E was run at a temperature of about 450° C. for about 5 hours. Table 14A shows the reaction temperature, time on stream (TOS), yields (in mole %) for each product, and Table 14B shows reaction temperature, TOS, and the conversion rate, and the 1,3-butadience selectivity:

TABLE 14A

Reaction Temperature, Time on stream (TOS), and product yields for Scheme E

| Temp (° C.) | TOS (hrs:mins:s) | Ethylene | Trans-2-butenes | 1-Butene | IsoButylene | Cis-2-butenes | 1,3-Butadiene |
|---|---|---|---|---|---|---|---|
| 450 | 0:23:43 | 0.119 | 38.722 | 24.927 | 0.206 | 28.491 | 7.535 |
| 450 | 1:10:44 | 0.13 | 37.997 | 24.819 | 0.196 | 28.026 | 8.593 |
| 450 | 1:57:43 | 0.129 | 38.005 | 24.671 | 0 | 28.076 | 8.873 |
| 450 | 2:44:43 | 0.127 | 37.943 | 24.42 | 0 | 28.202 | 9.05 |
| 450 | 3:31:42 | 0.125 | 37.984 | 24.25 | 0 | 28.257 | 9.119 |
| 450 | 4:18:40 | 0.131 | 38.054 | 24.106 | 0 | 28.32 | 9.117 |
| 450 | 5:05:39 | 0.168 | 38.39 | 23.929 | 0 | 28.866 | 8.379 |

TABLE 14B

Reaction Temperature, Time on stream (TOS), and product yields for Scheme E

| Temp (° C.) | TOS (hrs:mins:s) | Conversion | 1,3-BD Selectivity |
|---|---|---|---|
| 450 | 0:23:43 | 32.787 | 22.981 |
| 450 | 1:10:44 | 33.976 | 25.291 |
| 450 | 1:57:43 | 33.918 | 26.161 |
| 450 | 2:44:43 | 33.856 | 26.732 |
| 450 | 3:31:42 | 33.759 | 27.012 |
| 450 | 4:18:40 | 33.626 | 27.112 |
| 450 | 5:05:39 | 32.744 | 25.59 |

Table 15A shows the average yields for each product, and Table 15B shows the average conversion rate, and the average butadiene selectivity, based on the data points at the reaction temperature, based on the data from Tables 14A and 14B:

TABLE 15A

Average product yields for Scheme E

| # of data points, n= | Temp (° C.) | Ethylene | Trans-2-butene | 1-Butene | IsoButylene | Cis-2-butene | 1,3-Butadiene |
|---|---|---|---|---|---|---|---|
| 7 | 450 | 0.1327 | 38.1564 | 24.44611 | 0.057471 | 28.31987 | 8.666571 |

TABLE 15B

Average Conversion Rate and 1,3-BD Selectivity for Scheme E

| # of data points, n= | Temp (° C.) | Conversion | 1,3-BD Selectivity |
|---|---|---|---|
| 7 | 450 | 33.52372857 | 25.83977 |

As shown in Tables 14A, 14B, 15A, and 15B, increasing the amount of MgO catalyst from the 1 ml in Scheme A to the 2 ml in Scheme E did not show any advantages in the 5 hour test runs. However, the increase in the MgO catalyst is expected to reduce the deactivation rate of the $WO_3/SiO_2$ catalyst when the reaction is run for a longer time period.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method for producing 1,3-butadiene, comprising:
    receiving a feed stream comprising 2-butene; and
    contacting the feed stream with a catalyst bed in the presence of an oxidant to convert the 2-butene to 1,3-butadiene,
    wherein the catalyst bed comprises a first layer comprising tungsten oxide impregnated on an inorganic support, a second layer comprising magnesium oxide, and a third layer comprising tungsten oxide impregnated on an inorganic support, and
    wherein the first layer is upstream of the second layer and the third layer is downstream of the second layer such that the second layer is disposed between the first layer and the third layer.

2. The method of claim 1, wherein the feed stream does not include steam.

3. The method of claim 1, wherein the oxidant comprises air.

4. The method of claim 1, wherein the contacting is performed at a temperature in the range of 400° C. to 550° C.

5. The method of claim 1, wherein the feed stream comprises 1-butene.

6. The method of claim 1, wherein the inorganic support comprises silica.

7. The method of claim 1, wherein contacting the feed stream, at a temperature in the range of 400° C. to 550°, with a catalyst to convert the 2-butene to 1-3-butadiene achieves a 1,3-butadiene selectivity of at least 23%.

8. A method for producing 1,3-butadiene, comprising:

receiving a feed stream comprising 2-butene; and contacting the feed stream with a catalyst bed in the presence of an oxidant to convert the 2-butene to 1,3-butadiene, wherein the catalyst bed comprises a first layer comprising magnesium oxide and a second layer comprising tungsten oxide impregnated on an inorganic support, wherein the first layer is upstream of the second layer, wherein a volumetric ratio of the magnesium oxide to tungsten oxide impregnated on the inorganic support in the catalyst is in the range of 1:3 to 3:1, and wherein the contacting the feed stream with the catalyst to convert 2-butene to 1,3-butadiene achieves a 1,3-butadiene selectivity of at least 23%.

9. The method of claim 8, wherein the feed stream does not include steam.

10. The method of claim 8, wherein the oxidant comprises air.

11. The method of claim 8, wherein the contacting is performed at a temperature in the range of 400° C. to 550° C.

12. The method of claim 8, wherein the feed stream comprises 1-butene.

13. The method of claim 8, wherein the inorganic support comprises silica.

\* \* \* \* \*

UNITED STATES PATENT AND TRADEMARK OFFICE
CERTIFICATE OF CORRECTION

PATENT NO. : 10,407,363 B2
APPLICATION NO. : 15/678405
DATED : September 10, 2019
INVENTOR(S) : Alshafei et al.

Page 1 of 1

It is certified that error appears in the above-identified patent and that said Letters Patent is hereby corrected as shown below:

In the Claims

In Column 18, Line 54 should read:
-- and the third layer --

Signed and Sealed this
Fifth Day of November, 2019

Andrei Iancu
*Director of the United States Patent and Trademark Office*